United States Patent [19]

Marienne

[11] Patent Number: 5,423,855
[45] Date of Patent: Jun. 13, 1995

[54] CAPPED LOCKING CLAMP FOR MANIPULATION OF SURGICAL IMPLANTS

[75] Inventor: Jean-Luc Marienne, Berck sur mer, France

[73] Assignee: Sofamor, S.N.C., Rang du Fliers, France

[21] Appl. No.: 196,576

[22] Filed: Feb. 15, 1994

[51] Int. Cl.⁶ .............................................. A61B 17/28
[52] U.S. Cl. ................................... 606/208; 606/206
[58] Field of Search ............. 606/205, 208, 1, 206, 606/203, 210; 81/318

[56] References Cited

U.S. PATENT DOCUMENTS

| | | | |
|---|---|---|---|
| 3,911,925 | 10/1975 | Tillery, Jr. ...................... | 606/208 X |
| 4,192,314 | 3/1980 | Curutchet .......................... | 606/208 |
| 5,209,755 | 5/1993 | Abraham et al. ............... | 606/208 X |
| 5,236,436 | 8/1993 | Koros et al. ..................... | 606/208 X |
| 5,297,538 | 3/1994 | Daniel .............................. | 606/207 X |
| 5,308,357 | 5/1994 | Lichtman ........................... | 606/205 |

*Primary Examiner*—Stephen C. Pellegrino
*Assistant Examiner*—Nancy Mulcare
*Attorney, Agent, or Firm*—Woodard, Emhardt, Naughton, Moriarty & McNett

[57] ABSTRACT

Forceps with two pin-connected branches are provided with gripping noses on one end for manipulating surgical implants. The branches are spring biased apart but include a cap at the end remote from the gripping nose which is adapted to tilt and releasably retain the ends of the branches together beneath the cap. One of the branches is fixed within the cap while the other is insertable beneath the cap and has rounded edges to facilitate its insertion and removal. The tilting motion of the cap allows for temporary access of the inserted branch when it is desired to lock the branches together during manipulation of a gripped implant or the like.

10 Claims, 4 Drawing Sheets

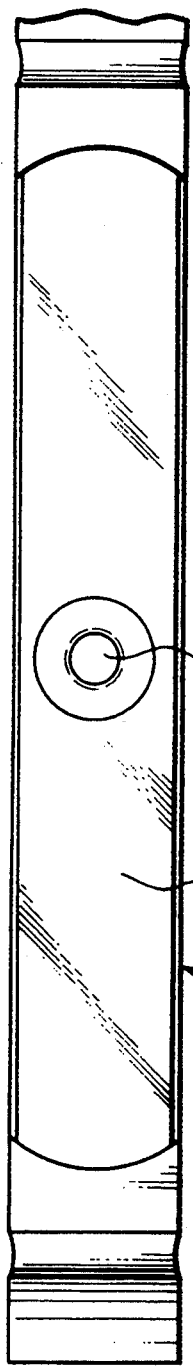
FIG.11
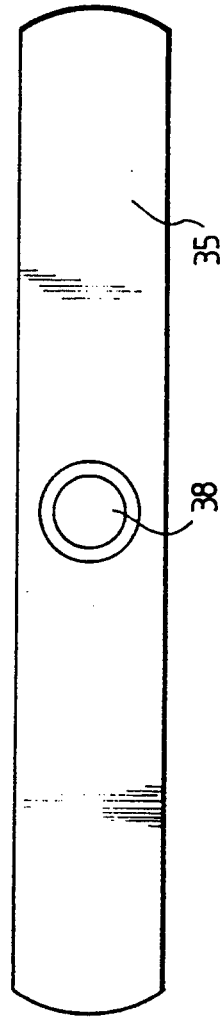
FIG.12
FIG.13
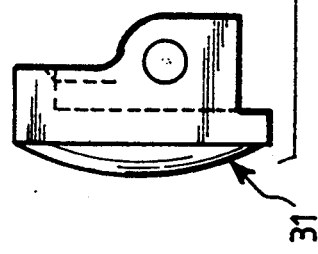

CAPPED LOCKING CLAMP FOR MANIPULATION OF SURGICAL IMPLANTS

The present invention relates to a forceps for handling surgical implants, in particular spinal osteosynthesis implants (screw or hook).

It is known that the various instruments for taking hold of and handling implants require the surgeon to exert sufficient force in the region of the noses of the instrument. Therefore, the instruments usually employed are in the form of forceps equipped with a rack. Now, around the gripping noses of these forceps and often over a great height, the overall size of the forceps is considerable. This overall size may constitute a hindrance which is all the more serious when the surgeon must use in turn several instruments close to one another and is unable, owing to their overall size, to dispose them within a radius of 3 or 4 centimetres on the vertebral segment of the patient.

Further, when the surgeon wishes to release the forceps, he must initially grip it still further so as to disengage the rack, which constitutes a further drawback.

An object of the invention is therefore to provide a forceps which is arranged in such a manner that these drawbacks are diminished or eliminated.

The forceps to which the invention relates comprises two branches articulated together and having terminal portions provided with gripping noses.

According to the invention, one end portion of one of the branches, opposed to the nose, is capped by a cap connected to an elastically yieldable device for retaining said cap on the branch while allowing said cap to tilt relative to the branch, and the corresponding end portion of the second branch is so shaped as to be insertable, by a transverse thrust, under the cap by causing it to tilt relative to the support branch therefor, said cap being thereafter automatically returned by the elastically yieldable device to a position in which it caps the two end portions of the branches and maintains the forceps in the closed position.

With this arrangement, the overall size of the forceps is markedly reduced relative to conventional rack-type forceps.

Further features and advantages of the invention will be apparent from the following description with reference to the accompanying drawings which illustrate two embodiments of the invention by way of non-limitative examples.

FIG. 11 is a partial top plan view of a branch of a second embodiment of the forceps according to the invention.

FIG. 12 is a partial side elevational view of the branch shown in FIG. 11 and the corresponding cap.

FIG. 13 is a top plan view of a removable wing member which is part of the branch shown in FIGS. 11 and 12.

Figure 1:
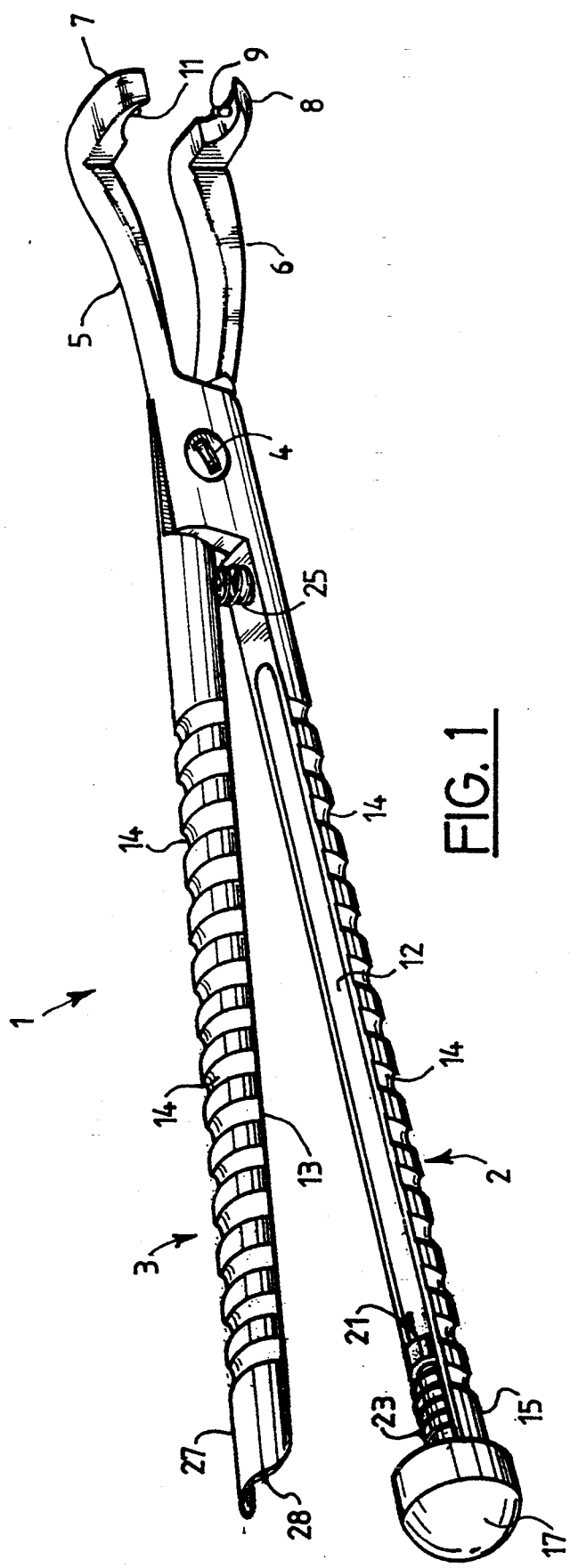
FIG. 1 is a perspective view to a slightly larger scale of a first embodiment of the forceps for gripping surgical implants according to the invention, in the open position.

The forceps 1 shown in the drawing is adapted to handle surgical implants, in particular spinal osteosynthesis implants such as screws and hooks having an open or closed body of various known types (not shown).

This forceps comprises two branches 2, 3 articulated together by a transverse pin 4 and having terminal portions 5, 6 provided with respective noses 7, 8 for taking hold of the implants. The noses 7, 8 are arranged in the known manner and comprise, in particular, on their confronting inner faces, two lugs 9, 11 for gripping the implant.

The portions of the branches 2, 3 remote from the noses 7, 8 beyond the articulation pin 4 have a substantially semi-circular cross-sectional shape with axial recesses 12, 13. Circular grooves 14 are provided on their outer surface so that the surgeon has a better grip on the forceps 1.

The end portion 15 of the branch 2 remote from the respective nose 7 terminates in a transverse eye 16 and is capped by a cap 17 made for example from a suitable plastics material. The cap 17 defines, adjacent the end portion 15, a cylindrical cavity 18 for receiving the eye 16 with, around the eye, a transverse clearance j on one side and a larger clearance J on the diametrically opposite side. The eye defines with the cavity 18 the clearance (J) between the edge 16a of the eye and the wall 18a of the cavity 18, the clearance (J) extending over a suitable angular sector around the eye 16, for example a semi-circumference.

Provided in the cap 17 is a tapped hole 20 extending axially relative to the branch 2 and adapted to receive a corresponding threaded end portion 19 of a screw 21 which extends with clearance through the central opening 22 of the eye 16. The screw 21 is partly disposed in the axial recess 12 and is provided with an elastically yieldable device constituted by a compression spring 23 coaxial with the shank of the screw 21. The spring 23 bears at one end against the eye 16 and at the opposite end against the head 24 of the screw 21. Consequently this spring exerts on the cap 17, through the screw 21, an axial force F for elastically returning the cap 17 to the position in which it bears against the surface of the eye 16 perpendicular to the axis of the recess 12.

Disposed in the vicinity of the articulation pin 4 between the two branches 2, 3 is a spring 25 whose opposite ends are respectively fixed to inner faces, planar in this region, of the branches 2 and 3. The spring 25 returns the latter to the spread-apart position, the forceps being open (position shown in FIG. 1).

Lastly, means are provided for limiting the angular opening of the branches 1, 2 when the forceps is in the open position.

In the embodiment shown in FIGS. 5 to 10, these means comprise, in the vicinity of the articulation pin 4, a lug 28 fixed to one of the branches, namely the branch 2 in the illustrated embodiment, and extending toward the confronting face of the other branch 3. Formed in this confronting face is a blind opening 29 whose section is larger than the section of the lug 28.

Figure 6:
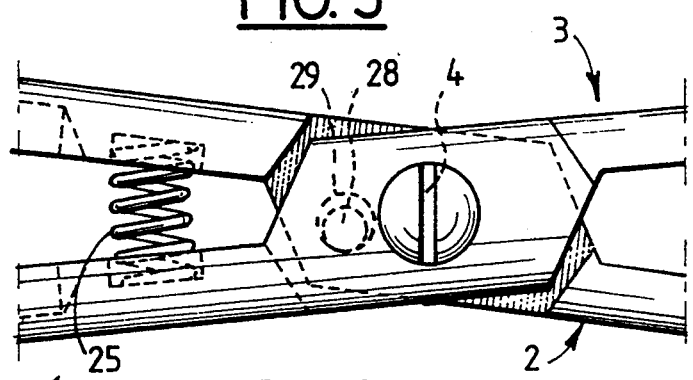
FIG. 6 is a view similar to FIG. 5 of the forceps in the open position.
Figure 7:
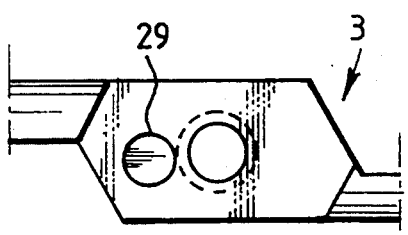
FIGS. 7 and 8 are respectively a top plan view and a side elevational view to a smaller scale of the articulation region of one of the branches of the forceps shown in FIGS. 5 and 6.
Figure 9:
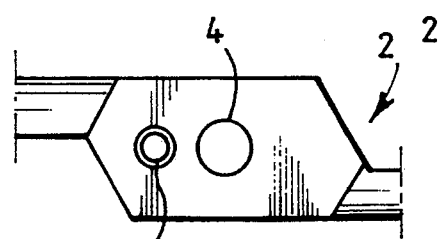
FIGS. 9 and 10 are views similar to FIGS. 7 and 8 of the other branch of the forceps.
Figure 8:
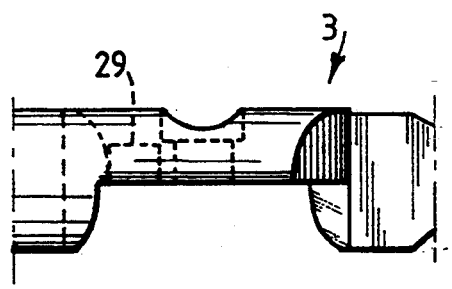
Figure 10:
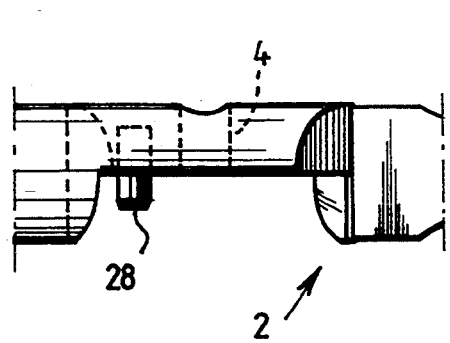

The latter therefore has a certain freedom of movement in the opening 29 when opening the forceps 1, depending on the respective dimensions of the lug and opening, which allows a correspondingly limited angular movement between the two branches 2, 3 when opening the forceps (FIG. 6).

The overall size of the forceps in the open position is consequently very small.

It should moreover be noted that the edge 26 of the cap 17 adjacent the ends of the branches 2, 3 is rounded in axial section and the end portion 27 of the branch 3 which is not provided with the cap 17 also has a rounded edge 28.

Figure 2:
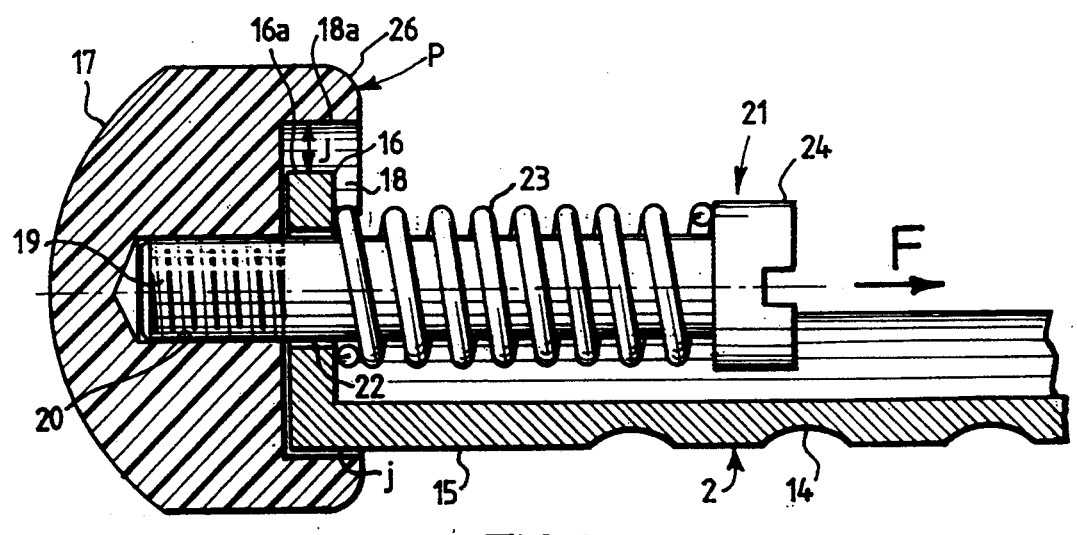
FIG. 2 is a longitudinal half-sectional, half-elevational view of the end portion of the branch shown in FIG. 1 provided with its maintaining cap and the elastically yieldable cap-retaining and returning device.
Figure 5:
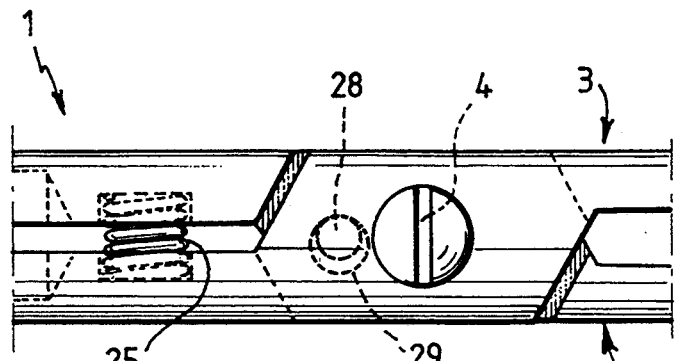
FIG. 5 is a partial side elevational view of the region of the articulation of the forceps shown in FIGS. 1 to 4, the forceps being in the closed position, this region being provided with means for limiting the angular opening of the forceps.

The handling forceps according to the invention is employed in the following manner:

In the open position, the branch 3 is maintained angularly spaced from the branch 2 by the spring 25, and the cap 17 solely caps the eye 16 and the end portion 15 of the branch 2, as shown in FIGS. 1 and 2.

Figure 3:
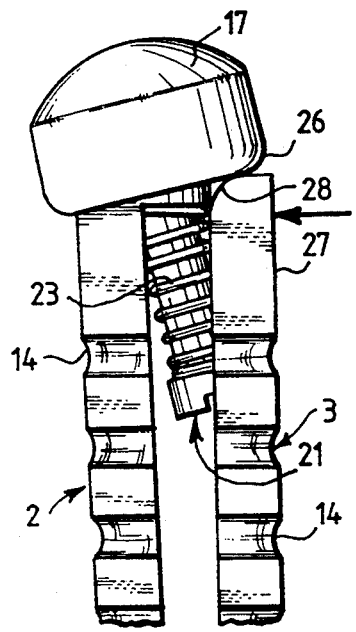
FIG. 3 is an elevational view to a larger scale than that of FIG. 1 of the end portions of the forceps in an intermediate position between the open and closed positions of the forceps.
Figure 4:
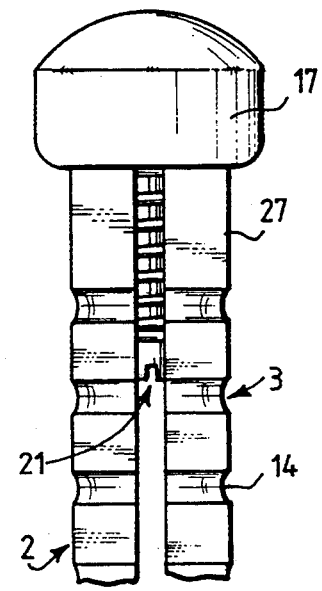
FIG. 4 is a view similar to FIG. 3 of the end portions of the forceps in the closed position of the latter, the two end portions of the branches being capped by the cap and the forceps being maintained in the closed position.

In starting in the open position shown in FIGS. 1 and 2, to close the forceps 1 it is sufficient to move the two branches 2, 3 towards each other until the end portion with the rounded edge 28 comes into contact with the corresponding rounded edge 26 of the cap 17 and lifts the latter (FIG. 3). The cap 17, the screw 21 and the spring 23 therefore tilt under the effect of this thrust owing to the provision of the clearance between the cap 17 and the eye 16. In continuing to exert the thrust on the end portion 27, the latter is engaged under the cap 17 in the semi-circular gap or clearance J between the eye 16 and the wall 18a which is so dimensioned as to receive the extremity of the end portion 27 of the branch 3 (FIG. 4). This tilting of the cap 17 and screw 21 occurs in opposition to the return force exerted by the spring 23 and, as soon as the extremity of the end portion 27 has completely entered the clearance J, the spring 23 automatically returns the cap 17 and screw 21 to their initial position (FIG. 4).

In this position, the noses 7, 8 are brought closer together and are clamped on the implant to be handled, the forceps 1 being maintained in this closed position by the cap 17.

To open the forceps, the surgeon merely has to exert with the thumb a slight pressure in a direction roughly parallel to the axis of the forceps 1 on the base of the cap 17 adjacent the rounded edge 26, which permits easily disengaging the latter from the end portion 27. As soon as the rounded edge 28 starts to slide on the rounded edge 26, the spring 25 swings the branch 3 away from the branch 2 to the open position of the forceps (FIG. 1). The lug 28 and the hole 29 limit the opening of the branches 2 and 3 to a small angle so that the opened forceps does not take up a large amount of space.

The overall size of the forceps 1 according to the invention is consequently smaller than that of the rack-type forceps of the prior art, so that the surgeon can hold several instruments close to one another in a region of very small area in the course of his intervention.

Further, the forceps is easily and rapidly released, i.e. opened, since it is sufficient to exert a slight thrust with a thumb or finger on the cap 17.

In the embodiment shown in FIGS. 11 to 13, the cap 31 is pivotally mounted on the forceps branch 32 by a transverse pin 33 mounted at the end of the latter, no cap returning spring being employed here. The cap 31 is therefore pivotable on the pin 33 between an open forceps position and a closed forceps position in which it caps the ends of the two branches.

Further, one of the branches of the forceps, namely the branch 32 in the presently-described embodiment, has a longitudinal recess 34. The latter forms a housing for an elongate wing member 35 which is rotatively mounted on this branch by a pin 36 engaged in apertures 37 and 38 in the branch 32 and the wing member 35.

The wing member 35 may assume two extreme angular positions, namely a first position in which it is entirely contained within the recess 34, its surface being then flush with the surface of the branch 32 that it completes, and a second position in which it is substantially perpendicular to the branch 32 and permits using the forceps as a screw driver.

It must be understood that the scope of the invention is not intended to be limited to the described embodiments and may encompass variants. Thus, the elastically yieldable device (21, 23) for returning the cap 17 may be made in any other way equivalent to that shown and the lugs 9, 11 may be eliminated.

What is claimed is:

1. Forceps for handling surgical implants, comprising a first branch, a second branch articulated with said first branch and and each branch having a terminal portion provided with a gripping nose and an opposite end portion, wherein the opposite end portion of the first branch is capped by a cap which is connected to the first branch by a retaining means for retaining said cap on the first branch while allowing said cap to move relative thereto, and wherein the opposite end portion of the second branch is so shaped as to fit under the cap, and further wherein the cap is movable relative to the first branch such that the second branch can be positioned under the cap with the first branch and be retained thereunder thus maintaining the forceps in a closed position.

2. Forceps according to claim 1, wherein said retaining means comprising a biasing spring means for drawing the cap to the opposite end portion of said first branch.

3. Forceps according to claim 2, wherein said first branch has an axial recess and a transverse terminal eye at its opposite end portion and said retaining means comprises a screw which is disposed in said axial recess of the first branch, and which extends through said transverse terminal eye and into the cap, wherein the cap caps the transverse eye with clearance, and wherein the biasing spring means is a compression spring which is coaxial with the screw and is compressed between the transverse terminal eye and the head of the screw, such that the biasing spring means exerts an elastically yieldable force through the screw on the cap to bias the cap to a position bearing against the transverse terminal eye.

4. Forceps according to claim 3 wherein the opposite end portion of the second branch has a rounded edge and the cap has a cavity with a perimeter wall; and wherein the transverse terminal eye of the first branch has walls and is mounted with said screw within the cavity of the cap such that there is a clearance between the wall of the cavity and a wall of the transverse terminal eye; and wherein the cap has rounded edges with are adjacent the opposite end portions of the first and second branches; and wherein the rounded edges of the cap and the rounded edges of the opposite end portion of the second branch cooperate to facilitate sliding of the opposite end portion of the second branch along the tilted cap and into the clearance region of the cavity which is defined by a suitable angular sector for receiving the second branch below the cap.

5. Forceps according to claim 1, wherein the cap is pivotally mounted on the first branch with a transverse pin about which said cap is pivotable from a position to permit opening the forceps to said closed position.

6. Forceps according to the 1, wherein both of the first and second branches have an inner face which faces the other branch and there is disposed in the vicinity of the articulation between the first and the second branch a biasing spring means having ends fixed to said inner faces of the first and second branches and biasing the first and second branches apart from one another.

7. Forceps according to claim 1, further comprising means for limiting the angular opening of the first and second branches.

8. Forceps according to claim 7, characterized in that each of the first and second branch have means comprise, in the vicinity of the articulation an inner face and said limiting thereof, a lug (28) fixed to the first branch and a blind opening provided in the inner face of the second branch for receiving the lug, the blind opening having a section which is larger than that of the lug so as to allow a limited angular displacement of the two branches relative to each other in the open position of the forceps.

9. Forceps according to claim 1, characterized in that the first branch has a rotary wing member pivotally mounted thereon, said wing member movable between a first position in which it is an extension of the first branch, and a second position in which it is substantially perpendicular to the first branch, so as to permit the forceps to be used as a screw driver.

10. Forceps according to claim 9, characterized in that the first branch has a longitudinal recess constituting a housing for the wing member, whereby the surface of the wing member is flush with that of the first branch when said wing member is within this housing.

* * * * *